(12) United States Patent
Del Curto et al.

(10) Patent No.: US 7,879,320 B2
(45) Date of Patent: *Feb. 1, 2011

(54) HYDROGEL INTERFERON FORMULATIONS

(75) Inventors: Maria Dorly Del Curto, San Quirico (IT); Ilaria Zambaldi, Parella (IT); Silvia Pompili, San Benedetto Del Tronto (IT); Pierandrea Esposito, Ivrea (IT)

(73) Assignee: Ares Trading S.A., Aubonne (CH)

( * ) Notice: Subject to any disclaimer, the term of this patent is extended or adjusted under 35 U.S.C. 154(b) by 184 days.

This patent is subject to a terminal disclaimer.

(21) Appl. No.: 11/596,599

(22) PCT Filed: May 13, 2005

(86) PCT No.: PCT/EP2005/052219

§ 371 (c)(1),
(2), (4) Date: Nov. 15, 2006

(87) PCT Pub. No.: WO2005/110466

PCT Pub. Date: Nov. 24, 2005

(65) Prior Publication Data

US 2007/0248674 A1  Oct. 25, 2007

Related U.S. Application Data

(60) Provisional application No. 60/579,218, filed on Jun. 14, 2004.

(30) Foreign Application Priority Data

May 17, 2004 (EP) ................... 04076496

(51) Int. Cl.
*A61K 38/21* (2006.01)
*A61K 38/19* (2006.01)
*C07K 14/52* (2006.01)

(52) U.S. Cl. ............. 424/85.6; 530/351; 424/85.1

(58) Field of Classification Search ............ None
See application file for complete search history.

(56) References Cited

U.S. PATENT DOCUMENTS

| 4,469,228 A | 9/1984 | Zupon et al. |
| 4,588,585 A | 5/1986 | Mark et al. |
| 4,695,623 A | 9/1987 | Stabinsky |
| 4,737,462 A | 4/1988 | Mark et al. |
| 4,879,111 A | 11/1989 | Chong |
| 4,897,471 A | 1/1990 | Stabinsky |
| 4,904,584 A | 2/1990 | Shaw |
| 4,959,314 A | 9/1990 | Mark et al. |
| 4,965,195 A | 10/1990 | Namen et al. |
| 5,017,691 A | 5/1991 | Lee et al. |
| 5,116,943 A | 5/1992 | Koths et al. |
| 5,541,293 A | 7/1996 | Stabinsky |
| 5,762,923 A | 6/1998 | Gross et al. |
| 5,858,001 A | 1/1999 | Tsals et al. |
| 6,013,253 A | 1/2000 | Martin et al. |
| 6,130,200 A | 10/2000 | Brodbeck et al. |
| 6,531,122 B1 | 3/2003 | Pedersen et al. |
| 6,569,420 B2 | 5/2003 | Chen et al. |
| 6,852,314 B1 | 2/2005 | Samaritani et al. |
| 6,923,956 B1 | 8/2005 | Tschope et al. |
| 2002/0172661 A1 | 11/2002 | Shirley et al. |
| 2003/0138491 A1* | 7/2003 | Tracy et al. .................. 424/486 |
| 2005/0186177 A1* | 8/2005 | Michael et al. ............. 424/85.6 |
| 2007/0059285 A1 | 3/2007 | Samaritani et al. |
| 2007/0092487 A1* | 4/2007 | Samaritani et al. ......... 424/85.6 |
| 2007/0104682 A1 | 5/2007 | Del Curto |
| 2007/0292391 A1 | 12/2007 | Samaritani et al. |

FOREIGN PATENT DOCUMENTS

| EP | 0098110 B1 | 1/1984 |
| EP | 0177153 B1 | 4/1986 |
| EP | 0509968 B1 | 10/1992 |
| EP | 736303 | 10/1996 |
| EP | 1224940 | 9/1998 |
| EP | 1250932 | 10/2002 |
| WO | WO 95/31213 | 11/1995 |
| WO | WO 99/55377 A3 | 11/1999 |
| WO | WO 00/24374 A1 | 5/2000 |
| WO | WO 01/03737 A1 | 1/2001 |
| WO | WO 01/58474 A2 | 8/2001 |
| WO | WO 02/03472 A2 | 1/2002 |
| WO | WO 02/09766 A1 | 2/2002 |
| WO | WO 02/51386 A2 | 7/2002 |
| WO | WO 03/066585 A2 | 8/2003 |
| WO | WO 2004/002404 A2 | 1/2004 |
| WO | WO 2005/117949 | 12/2005 |

OTHER PUBLICATIONS

Polman et al. 2000 BMJ 321: 490-494.*

(Continued)

*Primary Examiner*—Christine J Saoud
*Assistant Examiner*—Jegatheesan Seharaseyon
(74) *Attorney, Agent, or Firm*—Saliwanchik, Lloyd & Saliwanchik

(57) ABSTRACT

The present invention is related to pharmaceutical Poloxamer hydrogel formulations containing an interferon. In particular, the invention relates to sustained release hydrogel formulations of interferon-beta, method of preparation and use thereof.

20 Claims, 6 Drawing Sheets

OTHER PUBLICATIONS

Bromberg, L. E. et al. "Temperature-responsive Gels and Thermogelling Polymer Matrices for Protein and Peptide Delivery", *Advanced Drug Delivery Reviews*, 1998, pp. 197-221, vol. 31.

Chen-Chow, P.-C. et al. "In Vitro Release of Lidocaine from Pluronic F-127 Gels", *International Journal of Pharmaceutics*, 1981, pp. 89-99, vol. 8.

Derynck, R. et al. "Isolation and Structure of a Human Fibroblast Interferon Gene", *Nature*, Jun. 19, 1980, pp. 542-547, vol. 285.

Familletti, P. C. et al. "A Convenient and Rapid Cytopathic Effect Inhibition Assay for Interferon", *Methods in Enzymology*, 1981, pp. 387-394, vol. 78.

Gander, B. et al. "Crosslinked Poloxamers as a Versatile Monolithic Drug Delivery System", *Drug Devel. And Indust. Pharmacy*, 1986, pp. 1613-1623, vol. 12, Nos. 11-13.

Guzmán, M. et al. "Polyoxyethylene-polyoxypropylene Block Copolymer Gels as Sustained Release Vehicles for Subcutaneous Drug Administration", *International Journal of Pharmaceutics*, 1992, pp. 119-127, vol. 80.

Johnston, T. P. et al. "Sustained Delivery of Interleukin-2 from a Poloxamer 407 Gel Matrix Following Intraperitoneal Injection in Mice", *Pharmaceutical Research*, 1992, pp. 425-434, vol. 9, No. 3.

Katakam, M. et al. "Controlled Release of Human Growth Hormone in Rats Following Parenteral Administration of Poloxamer Gels", *Journal of Controlled Release*, 1997, pp. 21-26, vol. 49.

Mark, D. F. et al. "Site-specific Mutagenesis of the Human Fibroblast Interferon Gene", *Proc. Natl. Acad. Sci. USA*, Sep. 1984, pp. 5662-5666, vol. 81.

Miyazaki, S. et al. "Pluronic F-127 Gels as a Novel Vehicle for Rectal Administration of Indomethacin", *Chem. Pharm. Bull.*, 1986, pp. 1801-1808, vol. 34, No. 4.

Pestka, S. "Interferon Standards and General Abbreviations", *Methods in Enzymology*, 1986, pp. 14-23, vol. 119.

Rubinstein, S. et al. "Convenient Assay for Interferons", *Journal of Virology*, Feb. 1981, pp. 755-758, vol. 37, No. 2.

Schmolka, I. R. "A Review of Block Polymer Surfactants", *Journal of the American Oil Chemists' Society*, Mar. 1977, pp. 110-116, vol. 54.

Shepard, H. M. et al. "A Single Amino Acid Change in IFN-$\beta_1$ Abolishes its Antiviral Activity", *Nature*, Dec. 10, 1981, pp. 563-565, vol. 294.

Stewart, W. E. et al. "Interferon Nomenclature", *J. Interferon Res.*, 1980, pp. vi-vii, vol. 1.

Stratton, L. P. et al. "Drug Delivery Matrix Containing Native Protein Precipitates Suspended in a Poloxamer Gel", *Journal of Pharmaceutical Sciences*, Sep. 1997, pp. 1006-1010, vol. 86, No. 9.

Database WPI, Section Ch, Week 200406, Derwent Publicatons, Ltd., AN 2004-056676, XP-002301962 "Formulation for Injection of Interferon, Contains Interferon-alpha and Polyoxyethylene Polyoxypropylene Glycol", Dec. 3, 2003, 1 page.

Prisms Study Group "Randomised double-blind placebo-controlled study of interferon β-1a in relapsing/remitting multiple sclerosis" *The Lancet*, Nov. 7, 1998, pp. 1498-1504, vol. 352.

Clegg, A. et al. "Immunomodulatory drugs for multiple sclerosis: a systematic review of clinical and cost effectiveness" *Exp. Opin. Pharmacother.*, 2001, pp. 623-639, vol. 2, No. 4.

Hultgren, C. et al. "The antiviral compound ribavirin modulates the T helper (Th)1/Th2 subset balance in hepatitis B and C virus-specific immune responses" *Journal of General Virology*, 1998, pp. 2381-2391, vol. 79.

McCormick, J. B. et al. "Lassa Fever effective therapy with ribavirin" *The New England Journal of Medicine*, Jan. 2, 1986, pp. 20-26, vol. 314, No. 1.

Office Action dated Apr. 2, 2009 in U.S. Appl. No. 10/554,602.

Cook, S. D. "Advancing Treatment with Interferon beta-1b (Betaferon®/Betaseron®) in the Next Decade", *J. Neurol.*, 2003, pp. IV/15-IV/20, vol. 25, Suppl. 4.

Lam, X. M. et al. "The Effect of Benzyl Alcohol on Recombinant Human Interferon-γ", *Pharmaceutical Research*, 1997, pp. 725-729, vol. 14, No. 6.

Schuck, P. "Size-Distribution Analysis of Macromolecules by Sedimentation Velocity Ultracentrifugation and Lamm Equation Modeling", *Biophysical Journal*, Mar. 2000, pp. 1606-1619, vol. 78.

Wang, W. "Instability, Stabilization, and Formulation of Liquid Protein Pharmaceuticals", *International Journal of Pharmaceutics*, 1999, pp. 129-188, vol. 185.

Wang, Y.-C. J. et al. "Parenteral Formulations of Proteins and Peptides: Stability and Stabilizers", *Journal of Parenteral Science & Technology*, 1988, pp. S4-S26, vol. 42.

Office Action dated Mar. 27, 2009 in U.S. Appl. No. 11/597,987.

* cited by examiner

HYDROGEL INTERFERON FORMULATIONS

CROSS-REFERENCE TO RELATED APPLICATION

This application is the U.S. national stage application of International Patent Application No. PCT/EP2005/052219, filed May 13, 2005, which claims the benefit of U.S. Provisional Patent Application No. 60/579,218, filed Jun. 14, 2004, the disclosures of which are hereby incorporated by reference in their entireties, including all figures, tables and amino acid or nucleic acid sequences.

FIELD OF THE INVENTION

The present invention relates to pharmaceutical hydrogel formulations containing an interferon. In particular, the invention relates to sustained release hydrogel formulations of interferon-beta, method of preparation and use thereof.

BACKGROUND OF THE INVENTION

Recombinant protein pharmaceutics have already provided unique therapies for several previously untreated diseases and numerous new protein drugs are being developed.

Proteins are usually administered parenterally, which can lead to a rapid elimination of the protein from the circulation. In order to maintain therapeutically effective blood levels, it is often necessary to administer large or frequent doses. The inconvenience and potential adverse side effects of this approach might be circumvented by employing systems that provide sustained or controlled delivery of the protein.

Sustained delivery systems can achieve more constant blood levels of protein therapeutics than those obtained with bolus doses, leading to improved drug efficacy and fewer adverse side effects. Those drug delivery systems include injectable oils, emulsions, suspensions, liposomes, microparticulates (microcapsules or microspheres), implants or gel systems.

Among gel systems used in drug delivery, poloxamer gels are used for their unique property as thermoset gel-forming materials in situ. Poloxamers are block copolymers of poly (ethylene oxide) and poly(propylene oxide), well-known as non-ionic surfactants that form aqueous gels which undergo transitions from a low to a high viscous state as a consequence of an increase in temperature, called "thermal gelation".

In addition, Poloxamers possess good wetting, anti-foaming and solubilizing properties and are commonly used for pharmaceutical and medical purposes as drug delivery vehicles (Guzmán et al., 1992, *International Journal of Pharmaceutics*, 80, 119-127; Gander et al., 1986, *Drug Dev. and Indust. Pharmacy*, 12 (11-13), 1613-1623).

Poloxamers, referred by the trade name Pluronics® are tri-block copolymers having the following Formula (I):

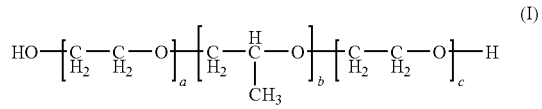

wherein (a) and (c) are statistically equal, (b) is equal or higher than 15 and (a+c) form 20 to 90% of the mass of the molecule.

The two polyethylene oxide chains (PEO) are hydrophilic while the polypropylene chain (PPO) is hydrophobic, giving to the PEO-PPO-PEO block copolymers amphiphilic properties that can be modulated by varying the numbers of units (a) and (b).

Due to their amphiphilic nature, PEO-PPO-PEO block copolymers are able to self-aggregate to form a variety of associated structures such as micelles and liquid crystalline phases, as well as microemulsions.

Among Pluronics®, Poloxamer 407 (Lutrol® F127 or Pluronic® F127), a poloxamer of Formula (I) wherein (a)=(c)=99 and (b)=65 and Poloxamer 338 (Lutrol® F108 or Pluronic® F108), a poloxamer of Formula (I) wherein (a)=(c)=16 and (b)=46 are known for their thermal gelation properties of their aqueous solutions in the 20-35% concentration (Guzmán et al., 1992, above). Particularly, a 22-25% (w/w) Poloxamer 407 polymer solution is liquid at relatively low temperatures, i.e. 4-10° C., but rapidly forms a highly viscous, firm gel upon warming above a characteristic transition temperature, i.e. 18-20° C. These gels have been used for example for liquid hydrogel formulations for sub-cutaneous injections, topical applications, aerosols that form a gel as it warms to body temperature (Guzmán et al., 1992, above).

Poloxamer 407 gels have been found to enhance the stability of proteins loaded into the gel matrix (Stratton et al., 1997, *Journal of Pharmaceutical sciences*, 86, 9, 1006-1010) and have been used for various formulations including Lidocaine (Chen-Chow et al., 1981, *International Journal of Pharmaceutics*, 8, 89-99), Indomethacin (Miyazaki et al., 1986, *Chem. Pharm. Bull.* 34(4), 1801-1808) and IL-2 (Johnston et al., 1992, *Pharmaceutical Research*, 9(3), 425-434).

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and anti-proliferative activity. On the basis of biochemical and immunological properties, the naturally occurring human interferons are grouped into three major classes: interferon-alpha (leukocyte), interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types might be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leukocyte and fibroblast IFN.

The interferon unit or international unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981, *J. Virol.*, 37, 755-758; Familletti et al., 1981, *Methods in Enzymology*, 78, Pestka Ed., Academic press, New York, 387-394). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, 1986, *Methods in Enzymology*, 78, Pestka Ed., Academic press, New York 119, 14-23).

Every class of IFN contains several distinct types. IFN-β and IFN-γ are each the product of a single gene.

The proteins classified as IFNs-α are the most diverse group, containing about 15 types. There is a cluster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. These new types of therapeutic agents can be sometimes called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al., 1980, *Nature*, 285, 542-547) deduced the complete amino acid sequence of the protein. It is 166 amino acid long.

Shepard et al., 1981, *Nature*, 294, 563-565 described a mutation at base 842 (Cys→Tyr at position 141) that abolished its anti-viral activity, and a variant clone with a deletion of nucleotides 1119-1121.

Mark et al., 1984, *Proc. Natl., Acad. Sci. U.S.A.*, 81(18), 5662-5666 inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

Rebif® (Serono—recombinant interferon-β), the latest development in interferon therapy for multiple sclerosis (MS) is interferon (IFN)-beta-1a produced from mammalian cell lines. Its recommended International Non-proprietary Name (INN) is "Interferon beta-1a".

Various formulations of IFNs with copolymers have been developed in the past decades. Among them, IFN alpha injection formulations containing polyoxyethylene polyoxypropylene glycol (JP 2003 342193), cyclaradine-IFN alpha combined formulations (EP 0177153), kits for interferon alpha room-temperature Poloxamers gels for topical administration (U.S. Pat. No. 4,469,228), microparticle formulations of IFNβ (WO 01/58474), compositions comprising glycoproteins chemically coupled with polyoxyethylene-polyoxypropylene copolymer (EP 0098110) and IFNβ formulations for mucosal, especially intra-nasal, delivery (WO 2004/002404) have been described.

As with all protein-based pharmaceuticals, one major challenge in the use of an interferon as a therapeutic agent, is to maintain a therapeutically effective dose in the blood level for a certain time without increasing the injected dose and the potential associated side effects. Consequently, there is a need for IFN pharmaceutical compositions that sustain IFN plasma levels for a longer period of time than liquid formulations and/or that provide a higher plasma exposure of IFN, thereby maintaining or improving IFN biological activity.

SUMMARY OF THE INVENTION

The present invention is directed to Poloxamer hydrogel or in-vivo forming Poloxamer gel pharmaceutical compositions that comprise an interferon (IFN), in particular recombinant h-IFNβ1a, and methods for their preparation. These pharmaceutical compositions are hydrogels prepared with Poloxamers, especially Poloxamer 407. Such pharmaceutical compositions are referred to herein as IFN "hydrogels" and they comprise an interferon (IFN) or an isoform, mutein, fused protein, functional derivative, active fraction thereof.

The poloxamer hydrogel IFN formulations of the invention have the advantage to be in-vivo forming gel that can be easily handled and that exhibit sustained release profile and/or higher bioavailability compared to bulk IFN formulations.

According to an embodiment of the present invention, the hydrogels further comprise at least one stabilizing agent.

According to another embodiment of the invention, the hydrogels further comprise at least one solution-to-gel temperature transition modifier as excipient.

In a first aspect, the invention provides a pharmaceutical composition comprising an interferon (IFN) or an isoform, mutein, fused protein, functional derivative or active fraction thereof, wherein said formulation is a Poloxamer hydrogel.

In a second aspect, the invention provides a method for preparing an IFN hydrogel formulation according to the invention, wherein said method comprises adding a calculated amount of poloxamer to a buffered solution at a temperature wherein a homogeneous polymer solution is formed and then adding the interferon or an isoform, mutein, fused protein, functional derivative, or active fraction thereof.

In a third aspect, the invention provides a use of an IFN-beta hydrogel formulation according to the invention for the preparation of a pharmaceutical preparation for the treatment of multiple sclerosis.

In a fourth aspect, the invention provides method for treating multiple sclerosis comprising the administration of a sustained release IFN-beta formulation according to the invention to a patient in need thereof.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

TFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. coli*, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

As used herein the term "muteins" refers to analogs of IFN in which one or more of the amino acid residues of a natural IFN are replaced by different amino acid residues, or are deleted, or one or more amino acid residues are added to the natural sequence of IFN, without changing considerably the activity of the resulting products as compared to the wild type IFN. These muteins are prepared by known synthesis and/or by site-directed mutagenesis techniques, or any other known technique suitable therefore. Preferred muteins include e.g. the ones described by Shepard et al., 1981, above or Mark et al., 1984, above.

Any such mutein preferably has a sequence of amino acids sufficiently duplicative of that of IFN, such as to have substantially similar or even better activity to an IFN. The biological function of interferon is well known to the person skilled in the art, and biological standards are established and available e.g. from the National Institute for Biological Standards and Control (http://immunology.org/links/NTBSC).

Bioassays for the determination of IFN activity have been described. An IFN assay may for example be carried out as described by Rubinstein et al., 1981, above. Thus, it can be determined whether any given mutein has substantially a similar, or even a better, activity than IFN by means of routine experimentation.

Muteins of IFN, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Gln, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |

TABLE I-continued

Preferred Groups of Synonymous Amino Acids

| Amino Acid | Synonymous Group |
|---|---|
| Asp | Glu, Asn, Asp |
| Glu | Asp, Lys, Asn, Gln, His, Arg, Glu |
| Met | Phe, Ile, Val, Leu, Met |
| Trp | Trp. |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp. |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met. |

Examples of production of amino acid substitutions in proteins which can be used for obtaining muteins of IFN, for use in the present invention include any known method steps, such as presented in U.S. Pat. Nos. 4,959,314, 4,588,585 and 4,737,46 to Mark et al.; U.S. Pat. No. 5,116,943 to Koths et al.; U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 to Shaw et al. Specific muteins of IFN-beta have been described, for example by Mark et al., 1984, above.

The term "fused protein" refers to a polypeptide comprising an IFN, or a mutein thereof, fused to another protein, which e.g., has an extended residence time in body fluids. An IFN may thus be fused to another protein, polypeptide or the like, e.g., an immunoglobulin or a fragment thereof.

"Functional derivatives" as used herein cover derivatives of IFN, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity IFN, and do not confer toxic properties on compositions containing it. These derivatives may, for example, include polyethylene glycol side-chains, which may mask antigenic sites and extend the residence of IFN in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of IFN, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

In accordance with the present invention, the use of recombinant IFN-beta 1a and the compounds of the invention is further particularly preferred.

A special kind of interferon variant has been described recently. The so-called "consensus interferons" are non-naturally occurring variants of IFN (U.S. Pat. No. 6,013,253). According to a preferred embodiment of the invention, the compounds of the invention are used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existent in that position in at least one naturally-occurring subtype. IFN-con encompasses but is not limited to the amino acid sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the sequence of IFN and the immunoglobulin sequence. The resulting fusion protein may have improved properties, such as an extended residence time in body fluids (half-life), increased specific activity, increased expression level, or the purification of the fusion protein is facilitated.

In a further preferred embodiment, IFN is fused to the constant region of an Ig molecule. Preferably, it is fused to heavy chain regions, like the $CH_2$ and $CH_3$ domains of human $IgG_1$, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO 99/55377, for example.

The dosage administered to an individual will vary depending upon a variety of factors, including pharmacokinetic properties, the route of administration, patient conditions and characteristics (sex, age, body weight, health and size), extent of symptoms, concurrent treatments, frequency of treatment and the effect desired.

Standard dosages of human IFN-beta 1a range from 80 000 IU/kg and 200 000 IU/kg per day or 6 MIU (million international units) and 12 MIU per person per day or 22 to 44 µg (microgram) per person. In accordance with the present invention, IFN-beta 1a may preferably be administered at a dosage of about 1 to 500 µg, more preferably of about 10 to 308 µg or about 10 to 260 µg per person, once a week or less.

The administration of active ingredients in accordance with the present invention may be by intra-muscular or sub-cutaneous route. The preferred route of administration for IFN is the subcutaneous route.

IFN may also be administered every two days, or less frequently. Preferably, IFN is administered once, twice or three times per week.

The preferred route of administration is subcutaneous administration, administered e.g. once a week or less.

Preferably the concentration of IFN-beta 1a in the formulation is at or about 10 µg/ml to at or about 800 µg/ml, more preferably at or about 20 µg/ml to at or about 500 µg/ml, more particularly preferably at or about 30 to at or about 300, most preferably at or about 44, 88 or 264 µg/ml.

The term "hydrogel" refers to a cross-linked network of hydrophilic polymers that possess the ability to organize itself in a three dimensional structure containing large amounts of water. Poloxamers are polymers that have the particularity to form micelles in aqueous solution. At higher concentrations and/or elevated temperature, Poloxamers undergo a "gelation" (solution-to-gel transition) by association of the micelles to form a liquid crystalline phase (gel) due to increasing inter-micellar interactions. Then, at still higher temperatures the gel melts again (Bromberg et al., 1998, *Advanced Drug Delivery Reviews* 31, 197-221).

The phase transition temperatures depend on the Poloxamer concentration in water. Typically, solution-to-gel transition occurs at temperatures from 5 to 30° C. and gel-to-solution transition at 35-50° C. over a range of polymer concentration from 20 to 30 wt %. Therefore, the term "Poloxamer hydrogel" according to the invention refers to a Poloxamer solution that has the property to exhibit a gelation (solution-to-gel transition) at the human body temperature. For example, Poloxamer hydrogels of the invention contain 20 to 30 wt % Poloxamer, typically 20 to 25 wt %. Therefore, the term "hydrogel" is also referred to an in-vivo forming gel.

The term "solution-to-gel (or "sol-gel") temperature transition modifier" refers to an excipient that is able to displace, preferably increase the solution-to-gel temperature transition of the IFN beta containing hydrogel. Examples of such modifiers are sugars such as Trehalose, polyethylene glycol, Glycerin such as Glycerol 30° and Cyclodextrins, preferably hydroxypropyl-β-cyclodextrin. A sol-gel temperature transition modifier can be used for example for increasing the temperature transition of the hydrogel around room temperature for increasing seringeability and/or storage temperature. Hydrogel according to the invention may contain for example about 1 to 3% w/w of sol-gel temperature transition modifier, preferably about 2.6% w/w.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Well known surfactants include polysorbates (Polyoxyethylene derivatives; Tween) as well as Pluronics.

According to one embodiment of the invention, Pluronics are surfactants that are preferably present in the stabilized IFN liquid formulation used for the preparation of hydrogels of the invention.

According to another embodiment, of the invention, Pluronics selected from Pluronic® F77 (Poloxamer 217), Pluronic® F87 (Poloxamer 237), Pluronic® F88 (Poloxamer 238) and Pluronic® F68 (Poloxamer 188), particularly preferably Pluronic® F68 (Pluronic® F68, BASF) are present in the stabilized IFN liquid formulation used for the preparation of hydrogels of the invention.

Pluronics are preferably present in the stabilized IFN liquid formulation at a concentration that is sufficient to maintain interferon stability over the desired storage period (for example 12 to 24 months) and also at a concentration that is sufficient to prevent protein losses due to adsorption on surfaces, such as the vial, ampoule or cartridge or the syringe. Typically, Lutrol F68: between 25 and 200 fold molar excess (respect to IFN), preferably 50 molar fold excess (about 3 mg/mL if the IFN loading is about 150 µg/mL)

Preferably, the concentration of Pluronics, particularly Pluronic® F68, in IFN liquid stabilized formulations is at or about 0.01 mg/ml to at or about 10 mg/ml, more preferably at or about 0.05 mg/ml to at or about 5 mg/ml, more particularly preferably at or about 0.1 mg/ml to at or about 2 mg/ml, most preferably at or about 1 mg/ml.

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisulfites, thiourea, methionine, salts of ethylenediaminetetraacetic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine.

Preferably, antioxidants and especially methionine are stabilizers that are present in the stabilized IFN liquid formulation used for the preparation of hydrogels of the invention. Typically, Methionine can be used between 100 and 800 fold molar excess (respect to IFN), preferably 400 fold molar excess (about 0.4 mg/mL if the IFN loading is about 150

Methionine can be present either in its free base form or in its salt form. Any stereoisomer (i.e., L, D, or DL isomer) of methionine may be used in the present method or formulation of the invention so long as methionine is present in its free base form or its salt form. Preferably, the L-stereoisomer is used. Analogues of methionine may also be used in the present formulation of the invention. The term "methionine analogue" refers to a derivative of the naturally occurring methionine. The methionine analogues can also be used in the present formulation in either their free base form or their salt form.

Increased and/or maintained stability with addition of antioxidants (e.g. methionine) occurs in a concentration dependent manner. That is, increasing concentrations of antioxidants lead to increased and/or maintained stability of the formulation containing interferon-beta of the present invention when that formulation containing interferon-beta normally exhibits oxidation or aggregate/oligomer formation in the absence of the antioxidant. Determination of the amount of an oxidant (e.g. methionine) to be used in the present formulation of the invention, in order to decrease oxidation or oligomer/aggregate formation, can readily be determined without undue experiment using methods generally known to one of skill in the art.

The term "bacteriostatic" refers to a compound or compositions added to a formulation to act as an anti-bacterial agent. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol.

Hydrogel formulations according to the invention may be mono-dose or multi-dose. Those liquid interferon formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Particularly preferred are phenol, benzyl alcohol and m-cresol, more preferred is benzyl alcohol. The bacteriostatic agent is used in an amount that will yield a concentration that is effective to maintain the formulation essentially bacteria free (suitable for injection) over the multi-dose injection period, which may be at or about 12 or 24 hours to at or about 12 days, preferably at or about 6 to at or about 12 days. The bacteriostatic is preferably present in a concentration of at or about 0.1% (mass bacteriostatic/mass of solvent) to at or about 2.0%, more preferably at or about 0.2% to at or about 1.0%. In the case of benzyl alcohol, particularly preferred are concentrations of 0.2 or 0.3%).

However, the use of a preservative, e.g. benzyl alcohol, is not limited to multi-dose formulations, but may also be added in mono-dose formulations. One embodiment of the present invention consists in single dose formulations containing benzyl alcohol.

Preferably, the formulations of the present invention have pH between about 3.0 and at or about 5.0, more preferably at or about 3.8-4.0. A preferred buffer is acetate, with preferred counter-ions being sodium or potassium ions. Acetate saline buffers are well known in the art. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 50 mM in acetate ions with a pH of 3.8.

The "cyclodextrins" contemplated for use herein are hydroxypropyl, hydroxyethyl, glucosyl, maltosyl and maltotriosyl derivatives of beta-cyclodextrin and the corresponding derivatives of gamma-cyclodextrin. The hydroxyalkyl groupings may contain one or more hydroxyl groups, e.g. hydroxypropyl (2-hydroxypropyl, 3-hydroxypropyl), dihydroxypropyl and the like. The glucosyl, maltosyl and maltotriosyl derivatives may contain one or more sugar residues, e.g. glucosyl or diglucosyl, maltosyl or dimaltosyl. Various mixtures of the cyclodextrin derivatives may be used as well, e.g. a mixture of maltosyl and dimaltosyl derivatives. Specific cyclodextrin derivatives for use herein include hydroxypropyl-beta-cyclodextrin (HPCD or HPBCD), hydroxyethyl-beta-cyclodextrin (HEBCD), hydroxypropyl-gamma-cyclodextrin (HPGCD), hydroxyethyl-gamma-cyclodextrin (HEGCD), dihydroxypropyl-beta-cyclodextrin (2HPBCD), glucosyl-beta-cyclodextrin ($G_1$-beta-CD or $G_1$BCD), diglucosyl-beta-cyclodextrin (2G $G_1$-beta-CD or 2 $G_1$BCD), maltosyl-beta-cyclodextrin ($G_2$-beta-CD or $G_2$BCD), maltosylgamma-cyclodextrin ($G_2$-gamma-CD or $G_2$GCD), maltotriosyl-beta-cyclodextrin ($G_3$-beta-CD or $G_3$BCD), maltotriosyl-gamma-cyclodextrin ($G_3$-gamma-CD or $G_3$GCD) and dimaltosyl-beta-cyclodextrin (2 $G_2$-beta-CD or 2 $G_2$BCD), and mixtures thereof such as maltosyl-beta-cyclodextrin/dimaltosyl-beta-cyclodextrin.

Hydroxypropyl-beta-cyclodextrin for use in the compositions of the present invention is commercially available and is a preferred cyclodextrin according to the invention.

The range of interferon in the formulations of the invention includes concentrations from about 1.0 μg/ml to about 50 mg/ml, although lower and higher concentrations are operable and are dependent on the intended delivery vehicle or route of administration, e.g. solution formulations will differ for trans-mucosal gels (e.g. IFN gel compositions for buccal or nasal route). The interferon concentration is preferably at or about 5.0 μg/ml to at or about 2 mg/ml, more preferably at or about 10 μg/ml to at or about 1 mg/ml, most preferably at or about 30 μg/ml to at or about 100 μg/ml.

Preferably the formulations of the invention retain at least at or about 60%, more preferably at least at or about 70%, most preferably at least at or about 80% of the interferon activity at the time of packaging over a period of 24 months.

The sustained release formulations of the present invention can be prepared by a process which comprises adding the calculated amounts of the interferon solution to the poloxamer homogeneous solution. The interferon solution is preferably an interferon stabilized solution, e.g. an interferon solution containing excipients such as stabilizers like L-Methionine, surfactants such as poloxamers, such as Poloxamer 188 or a combination thereof.

According to an embodiment of the invention, the formulations of the present invention may be further subjected to a filtration step under sterile conditions e.g. a sterilizing filtration using a 0.22 μm membrane carried out at a temperature wherein the viscosity of the poloxamer hydrogel is kept low, for example at 4° C.

In order to improve seringeability of the formulations of the present invention at room temperature, excipients that modify the solution-to-gel transition temperature of poloxamer hydrogel can be added, preferably to the buffer solution before the formation of the liquid hydrogel solution, i.e. before the addition of poloxamer. Examples of excipients that modify the sol-gel transition temperature of poloxamer hydrogel are polyethylene glycol, Glycerin such as Glycerol 30°, sugars such as Trehalose and Cyclodextrins, such as hydroxypropyl-β-cyclodextrin.

According to one embodiment of the invention, the hydrogel formulation has a viscosity at 4° C. between the viscosity of water and 200 mPas range, preferably in a range between 100-150 mPas that could be included in special devices such as auto-injectors or pre-filled syringes and could form an "in situ" gel after subcutaneous injection.

The resulting solution is then placed in vials, ampoules, cartridges or pre-filled syringes. Variations of this process would be recognized by one of ordinary skill in the art. For example, the order in which the components are added, whether additional additives are used, the temperature and pH at which the formulation is prepared, are all factors that may be optimised for the concentration and means of administration used.

The preserved formulations may be provided to patients as clear solutions as storage is preferably carried out under the sol-gel transition temperature of the hydrogel.

The interferon in hydrogel formulations described herein, may be administered to a patient in accordance with the present invention via a variety of delivery methods including subcutaneous injection, transmucosal, implant, or other means appreciated by the skilled artisan, as well-known in the art.

The term "vial" refers broadly to a reservoir suitable for retaining sustained release interferon formulation of the invention in solid or liquid form in a contained sterile state. Examples of a vial as used herein include ampoules, cartridges, blister packages, or other such reservoir suitable for delivery of the interferon to the patient via syringe or transmucosal spray.

The formulations according to the invention can also be marketed as pre-filled syringes.

The formulations of the invention can be administered using recognized injection devices. Examples comprising these single vial systems include auto-injector or pen-injector devices for delivery of a solution such as Rebiject®.

Needles for injection devices are selected to match with the thickness of the hydrogel of the invention. For example, the hydrogel of the invention can be injected with injection devices having different needle gauges such as 18/23 (internal diameter equivalent to a 18 gauge needle and minimum external diameter of a 21 gauge needle) or 21/26 (internal diameter equivalent to a 21 gauge needle and minimum external diameter of a 26 gauge needle).

Preferably, the formulations of the invention can be administered using recognized devices for hydrogels. For Example, Depot One Needle injection technology (Imprint Pharmaceuticals) can be used for injecting hydrogels of the invention.

The term "treatment" within the context of this invention refers to any beneficial effect on progression of disease, including attenuation, reduction, decrease or diminishing of the pathological development after the onset of the disease.

Pharmaceutical compositions of the invention comprising IFN or an isoform, mutein, fused protein, functional derivative, active fraction or salt are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including multiple sclerosis; autoimmune diseases, including rheumatoid arthritis, psoriasis, Crohn's disease; and cancers, including breast, prostate, bladder, kidney and colon cancers.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skilled in the art.

According to one embodiment, the invention provides a pharmaceutical composition, wherein said formulation is a Poloxamer hydrogel comprising an interferon-beta.

In a further embodiment, the invention provides a pharmaceutical composition, wherein said composition is a Poloxamer hydrogel comprising recombinant interferon-beta such as recombinant interferon-beta 1a.

In another embodiment, the invention provides a pharmaceutical composition according to the invention, wherein said composition further comprises a buffer and an anti-oxidant.

In another embodiment, the invention provides a pharmaceutical composition according to the invention, wherein said composition further comprises a buffer and a surfactant.

According to another embodiment, the invention provides a pharmaceutical composition according to the invention, wherein said composition further comprises a sol-gel temperature transition modifier.

According to a further embodiment, the invention provides a pharmaceutical composition according to the invention, wherein said composition further comprises a sol-gel temperature transition modifier selected from Trehalose and a Cyclodextrin.

According to one embodiment, the invention provides a pharmaceutical composition, wherein said formulation is a Poloxamer 407 hydrogel.

In a further embodiment, the invention provides a pharmaceutical composition, wherein said composition is a Poloxamer 407 hydrogel which comprises about 20 to 25% w/w Poloxamer 407.

According to one preferred embodiment, the invention provides a pharmaceutical composition, wherein said formulation comprises recombinant interferon-beta, such as recombinant interferon-beta 1a, an acetate buffer and L-methionine as anti-oxidant.

According to another preferred embodiment, the invention provides a pharmaceutical composition, wherein said formulation is a Poloxamer 407 hydrogel comprising recombinant interferon-beta, such as recombinant interferon-beta 1a, an acetate buffer, L-methionine as anti-oxidant and Poloxamer 188 as surfactant.

According to another preferred embodiment, the invention provides a pharmaceutical composition, wherein said formulation is a Poloxamer 407 hydrogel comprising recombinant interferon-beta, such as recombinant interferon-beta 1a, an acetate buffer, L-methionine as anti-oxidant, Poloxamer 188 as surfactant and Trehalose as sol-gel temperature transition modifier.

According to another preferred embodiment, the invention provides a pharmaceutical composition, wherein said formulation is a Poloxamer 407 hydrogel comprising recombinant interferon-beta, such as recombinant interferon-beta 1a, an acetate buffer, L-methionine as anti-oxidant and a Cyclodextrin as sol-gel temperature transition modifier, preferably hydroxypropyl beta Cyclodextrin.

According to another preferred embodiment, the invention provides a pharmaceutical composition selected from the following group:
  Poloxamer 407—25% w/w
  Acetate buffer 50 mM/pH 3.8—74.7% w/w
  r-h-IFNbeta 1a—0.012% w/w
  L-Methionine—0.03% w/w
  Poloxamer 188—0.24% w/w;

Poloxamer 407—25% w/w
  Acetate buffer 50 mM/pH 3.8—72.04% w/w
  r-h-IFNbeta 1a—0.012% w/w
  L-Methionine—0.03% w/w
  Poloxamer 188—0.24% w/w
  Trehalose—2.6% w/w;

Poloxamer 407—20% w/w
  Acetate buffer 50 mM/pH 3.8—77.34% w/w
  r-h-IFNbeta 1a—0.015% w/w
  L-Methionine—0.04% w/w
  Hydroxypropyl-β-Cyclodextrin—2.6% w/w;

Poloxamer 407—25% w/w
  Acetate buffer 50 mM/pH 3.8—72.04% w/w
  r-hIFNbeta 1a—0.012% w/w
  L-Methionine—0.03% w/w
  Poloxamer 188—0.24% w/w
  Glycerol 30°Bé—2.6% w/w;

And
  Poloxamer 407—25% w/w
  Acetate buffer 50 mM/pH 3.8—72.04% w/w
  r-hIFNbeta 1a—0.012% w/w
  L-Methionine—0.03% w/w
  Poloxamer 188—0.24% w/w
  PEG (Lutrol®E400)—2.6% w/w.

In another embodiment, the invention provides a method for preparing an IFN hydrogel pharmaceutical composition according to the invention, wherein said method comprises adding a calculated amount of Poloxamer to a buffered solution at a temperature wherein a homogeneous polymer solution is formed and then adding the interferon or an isoform, mutein, fused protein, functional derivative, or active fraction thereof.

In a further embodiment, the invention provides a method for preparing an IFN hydrogel pharmaceutical composition according to the invention, wherein the buffer solution contains a sol-gel temperature transition modifier selected from Trehalose and cyclodextrin, preferably Hydroxypropyl-β-Cyclodextrin.

In another further embodiment, the invention provides a method for preparing an IFN hydrogel pharmaceutical composition according to the invention, wherein the interferon is added from a solution containing stabilizers, preferably selected from L-Methionine and Poloxamer 188 and a combination thereof.

In a further embodiment, the invention provides a use of an IFN-beta hydrogel according to the invention for the preparation of a pharmaceutical composition for the treatment of multiple sclerosis.

In a further embodiment, the invention provides a method for the treatment of multiple sclerosis comprising the administration of an IFN-beta hydrogel according to the invention to a patient in need thereof.

The invention will now be described by means of the following Examples, which should not be construed as in any way limiting the present invention. The Examples will refer to the Figure specified here below.

EXAMPLES

Figure 1:
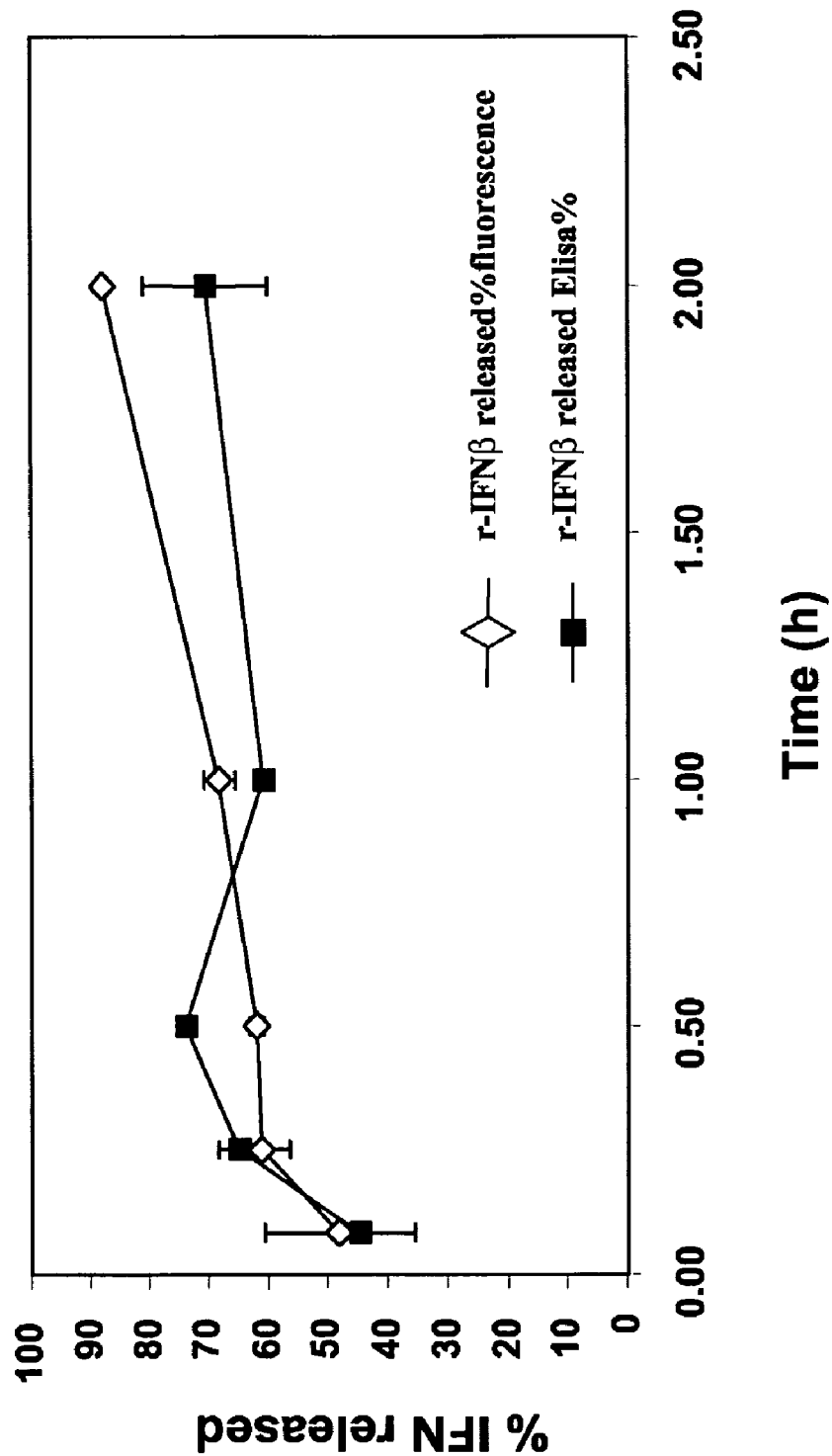
FIG. 1 shows the percentage of r-hIFNβ 1a release from the r-hIFNβ 1a Poloxamer Hydrogel (1) in PBS at pH 7.4 at 37° C. measured by SE-HPLC/fluorescent detector (lozenges) and Elisa assay (full squares) versus time after hydrogel injection in PBS (Example 1).

The following abbreviations refer respectively to the definitions below:

cm (centimeter), cps (centipoises), Da (Dalton), g (gram), µg (microgram), min (minute), mg (milligram), mL (milliliter), mm (millimeter), mM (millimolar), mPas (millipascal seconds), rpm (rotation per minute), nm (nanometer), CHO (Chinese Hamster Ovary), IFN (interferon), IU (International Units), i.v. (intra-venous), EMEM (Minimum Essential Medium Eagle with Earle's salts), FBS (Fetal Bovine Serum), GMS (Glyceryl monostearate), MTT (N-2-hydroxyethylpiperazine-N'-2-ethanesulfonic acid), MS (multiple sclerosis), MW (molecular weight), PBS (Phosphate Buffered Saline), PES (polyethersulfone), PP (polypropylene), PVDF (polyvinylidene fluoride), r-IFN beta (recombinant interferon beta), r-hIFNβ 1a (recombinant interferon beta 1a produced in CHO cells), RIA (Radioimmuno-assay), s.c. (Subcutaneous), TIW (Three times a week), UI (International unit), VSV (Vesicular Stomatitis Virus).

Synthesis of Poloxamers is described in Schmolka 1977, Journal of the American Oil Chemist's Society 54, 110-116 and are commercially available.

Example 1

Poloxamer 407-r-hIFN-β 1a Hydrogel (1)

1. General Preparation Procedure:

In a polypropylene becker (low protein adsorption) placed in an ice bath, a weighed amount of Lutrol® F127 is slowly added to cold (2-8° C.) acetate buffer [50 mM, pH 3.8] under magnetic stirring [at 500-800 rpm] until complete dissolution of the polymer.

In a different vessel, a small amount of acetate buffer, containing stabilizing agents (eg. Lutrol® F68 and L-Methionine), is added to a concentrated r-IFN-beta bulk solution (2 mg/mL). This formulated buffer is added into the polymer solution, reducing the stirring to 100-200 rpm, to minimize the mechanical stress of the protein. The final formulation is filled into Polypropylene syringes at 2-8° C.

The r-IFN-beta bulk solution, is an acetate buffer solution, concentrated from 0.348 mg/mL to 2 mg/mL by ultra-filtering centrifugation (Sartorius VivaSpin 20 mL, MW cut off 5000 Da, 2500 rpm). Concentrated bulk solution is always analysed by current SEC-HPLC method for assay and purity (% of monomer) as described in Example 1 §5 below.

2. r-hIFN-beta

Rebif® bulk 0.348 mg/mL was used and a stabilized solution of r-hIFN-beta 1a was prepared according to the general procedure under §1 above by addition of a combination of stabilizers, e.g. Lutrol® F68/L-Methionine.

3. Excipients:

3.1. Lutrol F127® (Poloxamer, Pluronic, Synperonic)

Lutrol F127 (polyoxyethylen-polyoxypropylene-polyoxyethylen tri-block copolymer) BASF is a Block Copolymer of poly-ethylene-oxide and poly-propylene-oxide. Included in the FDA inactive Ingredients Guide (i.v. injections, inhalations, ophthalmic preparations, oral powder, solutions, suspensions and syrup, also topical preparations). Included in non-parenteral medicines licensed in the UK. European Pharmacopoeia 4, p. 1777; USP 24 NF19 p 2492-2493.

In Pluronic® F127, the percentage of polyoxyethylene (hydrophilic) is 73%, (a poloxamer of Formula (I) wherein (a)=(c)=67 and (b)=98).

Typical properties of Pluronic® F127 are listed below:
Average Molecular Weight: 12600 g/mol
Melt. point: 56° C.
Physical Form @ 20° C.: solid
Viscosity @ 77° C.: 3100 cps
Surface tension @ 25° C. 0.1% conc.: 41 dynes/cm
Draves Wetting (3 gm hook, 0.1% conc. @ 25° C.: >360 s
Foam Height (Ross Miles, 0.1%, aqueous @ 50° C.: 40 mm
Cloud point in aqueous solution, 1% conc.: >100° C.
HLB (hydrophile-lipophile balance) in water at 25° C.: 18-23
Solubility in water @ 25° C.: >10%.

3.2. Glacial Acetic Acid, Sigma 3.3. Lutrol® F68 (Poloxamer, Pluronic, Synperonic)

Lutrol F68 (polyoxyethylene-polyoxypropylene block copolymer), BASF is a Block Copolymer of poly-ethylene-oxide and poly-propylene-oxide. Included in the FDA inactive Ingredients Guide (i.v. injections, inhalations, ophthalmic preparations, oral powder, solutions, suspensions and syrup, also topical preparations). Included in non-parenteral medicines licensed in the UK. European Pharmacopoeia 4, p 1777; USP 24 NF19 p 2492-2493.

In Pluronic® F68, the percentage of polyoxyethylene (hydrophilic) is 80%, and the molecular weight of the polyoxypropylene (hydrophobic) is approximately 1,967 Da (a poloxamer of Formula (I) wherein (a)=(c)=79 and (b)=28).

Typical properties of Pluronic F68 are listed below:
Average Molecular Weight: 8400;
Melt/pour point: 52° C.;
Physical Form @ 20° C.: solid;
Viscosity (Brookfield) cps: 1000 [liquids at 25° C., pastes at 60° C. and solids at 77° C.];
Surface tension, dynes/cm @ 25° C.;
  0.1% Conc.: 50.3
  0.01% Conc.: 51.2

0.001% Conc.: 53.6
Interfacial tension, dynes/cm @ 25° C. vs Nujol;
   0.1% Conc.: 19.8
   0.01% Conc.: 24.0
   0.01% Conc.: 26.0
Draves Wetting, Seconds 25° C.
   1.0% Conc.: >360
   0.1% Conc.: >360
Foam Height
   Ross Miles, 0.1%, mm @ 50° C.: 35
   Ross Miles, 0.1%, mm @ 26° C.: 40
   Dynamic, 0.1%, mm @ 400 ml/min: >600
Cloud point in aqueous solution, ° C.
   1% Conc.: >100
   10% Conc.: >100
HLB (hydrophile-lipophile balance): 29.

3.4. L-Methionine, Sigma

L-Methionine (L-Met) is included in the formulation at a level of 0.03% to limit oxidation and therefore IFN-beta solution stability.

4. Hydrogel (1) Composition

A hydrogel (1) containing 120 μg/ml of r-hIFN-beta 1a was prepared having the following composition:

| | |
|---|---|
| Lutrol ® F127 | 25.0% w/w |
| Acetate buffer [50 mM/pH 3.8] | 74.7% w/w |
| r-hIFN beta 1a | 0.012% w/w |
| L-Methionine | 0.03% w/w |
| Lutrol ® F-68 | 0.24% w/w |

The hydrogel (1) was manufactured according to the general procedure from Example 1, §1 and wherein 25 g of Lutrol® F127 solution and 3 mg of r-hIFN-beta 1a were used.

5. Physico-Chemical Characteristics

Viscosity

Dynamic viscosity studies were performed to characterize such the hydrogel and to support a suitable injectability protocol; A viscoStar L Fungilab rotational viscometer was used, obtaining a direct reading of viscosity in mPas (centipoises). A 50 g batch of hydrogel (1) was prepared and introduced into a polypropylene vial, kept in ice bath (T=5±2° C.) during the viscosity analysis. The reported viscosity values range between 100-140 mPas (spindle n° 2, spindle rate of 100 rpm and 3 minutes equilibrating time).

Protein Release

To simulate physiological subcutaneous conditions, IFN-beta release from hydrogel (1) was investigated in PBS. Drug release test were performed using 1 g of formulation (1) (dispensed using pre-filled syringes) into 4 mL of PBS pH 7.4 at 37±2° C. (shaker bath speed=100 rpm). Samples collected at: 5, 15, 30 minutes, 1 and 2 hours. Each sample was analyzed by SE-HPLC with fluorescent detector (Trp fluorescence) and confirmed by ELISA method (Toray Kit). These methods are detailed below.

The amount of IFN-beta detected in the medium was expressed as a percentage of total protein released. Release profiles obtained with the two methods indicate a biphasic release pattern, with a fast onset phase followed by a slower drug release rate (FIG. 1).

Extraction Procedure and SE-HPLC Analysis:

Tests were performed to optimise the extraction method of IFN-beta incorporated into the hydrogels systems, and to measure drug recovery.

An extraction procedure was set up as follows, based on a water/organic solvent mixture composed by water and acetone:

500 mg of hydrogel formulation (1) were dissolved in 1.0 mL of acetone in a centrifuge tube and sonicated for 2 minutes in ultrasonic bath at less than 10° C.

water was added up to 3 mL as final volume the sample obtained was centrifuged (5 minutes at 10.000 rpm, at +4° C.)

the liquid phase was collected and analysed

After the extraction procedure, samples were analysed by SE-HPLC with the following operative conditions:

HPLC column TSK G2000 SW$_{XL}$ cod. 08540 (7.8 mm ID×30 cm, 5μ)

injection volume 100 μL column temperature room temperature sample temperature room temperature flow rate: 0.5 mL/min. (isocratic)

mobile phase 70% v/v purified water (MILLIQ-Millipore)-30% v/v acetonitrile-0.2% v/v TFA run time 27 min equilibration time 3 min fluorescence detector wavelengths: excitation 280 nm, emission 348 nm.

ELISA Test:

An ELISA immunoassay (Toray kit) was used in order to assess the concentration of IFN-beta released by IFN hydrogel (1). This assay employs the one-step sandwich method and is based on the 96-well microplates coated with polyclonal antibody to r-hIFN-beta. An enzyme-linked monoclonal antibody specific for r-hIFN-beta is added to the wells and then standards and samples are pipetted into the wells; any r-hIFN-beta present is bound by immobilized antibody. Following a wash to remove any unbound antibody-enzyme reagent, a substrate solution is added to the wells and color develops in proportion to the amount of r-hIFN-beta bound in the initial step. The color development is stopped and the intensity of the color is measured.

The assay was performed according to the leaflet with the difference that the sample incubation is made overnight at +4° C.

The antibody-coated microplate was washed with 400 μL of washing solution and dried on a paper. Then, 50 μL/well of the enzyme-labelled antibody were added to the microplate previously filled with 100 μL of sample coming from drug release experiments from hydrogel (1) or with r-hIFN-beta reference (bulk) concentration-curve (0-200 IU/mL). The microplate was covered and shacked thoroughly while incubating for 120 minutes at room temperature. At the end of the incubation, samples were removed, the microplate was washed 3 times and dried on a paper. 100 μL of colour developer solution was added into each well; after 30 min incubation, 100 μL of stopper reaction were added and the absorbance was read at double wavelengths of 450 nm and 650 nm (FIG. 1).

Preliminary Stability

IFN hydrogel (1) stability was monitored at t=0, 24 h, 1 week, 1 and 2 months at 4° C. The analysis performed were: drug loading by visual inspection and viscosity (spindle n° 2, 100 rpm, T=6±2° C.).

The hydrogel (1) formulation was stable over at least 2 months.

Example 2

Bioactivity of Poloxamer 407-r-hIFN-beta 1a Hydrogel (1)

The biological activity of hydrogel (1) is measured through the antiviral activity of r-hIFN-beta 1a released from hydrogel (1) formulation compared to the antiviral activity observed with bulk IFN-beta.

Vesicular stomatitis virus (VSV), a virus that causes a disease of the hoof and mouth in livestock was chosen for use in this study because of its sensitivity to interferons.

The antiviral assay used is based on the IFN-beta induced inhibition of viruses cytopathic effect on lines of WISH cells, plated in EMEM containing 5% FBS at $4 \times 10^4$ cells/well (50 µL/well) of a 96-well microtiter plate previously filled with serial dilution (1:1.5 dilution) of r-hIFN-beta hydrogel sample, or r-hIFN-beta 1a reference (bulk). Cells were incubated for 18-22 hours at 37° C. and 5% $CO_2$ before the addition of 50 µl/well of Vesicular Stomatitis Virus (VSV) suspension prepared in EMEM containing 2.5% FBS. Control cell wells received medium alone and no virus suspension whereas control virus wells received VSV suspension alone. Infected cells were incubated for further 20-24 hours at 37° C. and 5% $CO_2$ and then stained with a 5% MTT solution for 2 hours. At the end of the experiment, supernatants were discarded and formazan salts were dissolved by the addition of 200 µL/well of ethanol 96%. The plates were read at 595 nm in the spectrophotometer plate-reader. Results were expressed as the percentage of cytopathic effect inhibition vs control cells.

The in vitro biological activity of r-hIFN-beta 1a, released from hydrogel (1) formulation after 2 hours, was evaluated using the WISH-assay described above in two different sets of experiment. The concentration in r-hIFN-beta 1a was 37.7 µg/mL. Any possible interference of the Lutrol hydrogel without r-hIFN-beta 1a (placebo) used for the preparation of the hydrogel was also verified by spiking the r-hIFN-beta 1a bulk in the placebo.

Figure 2:
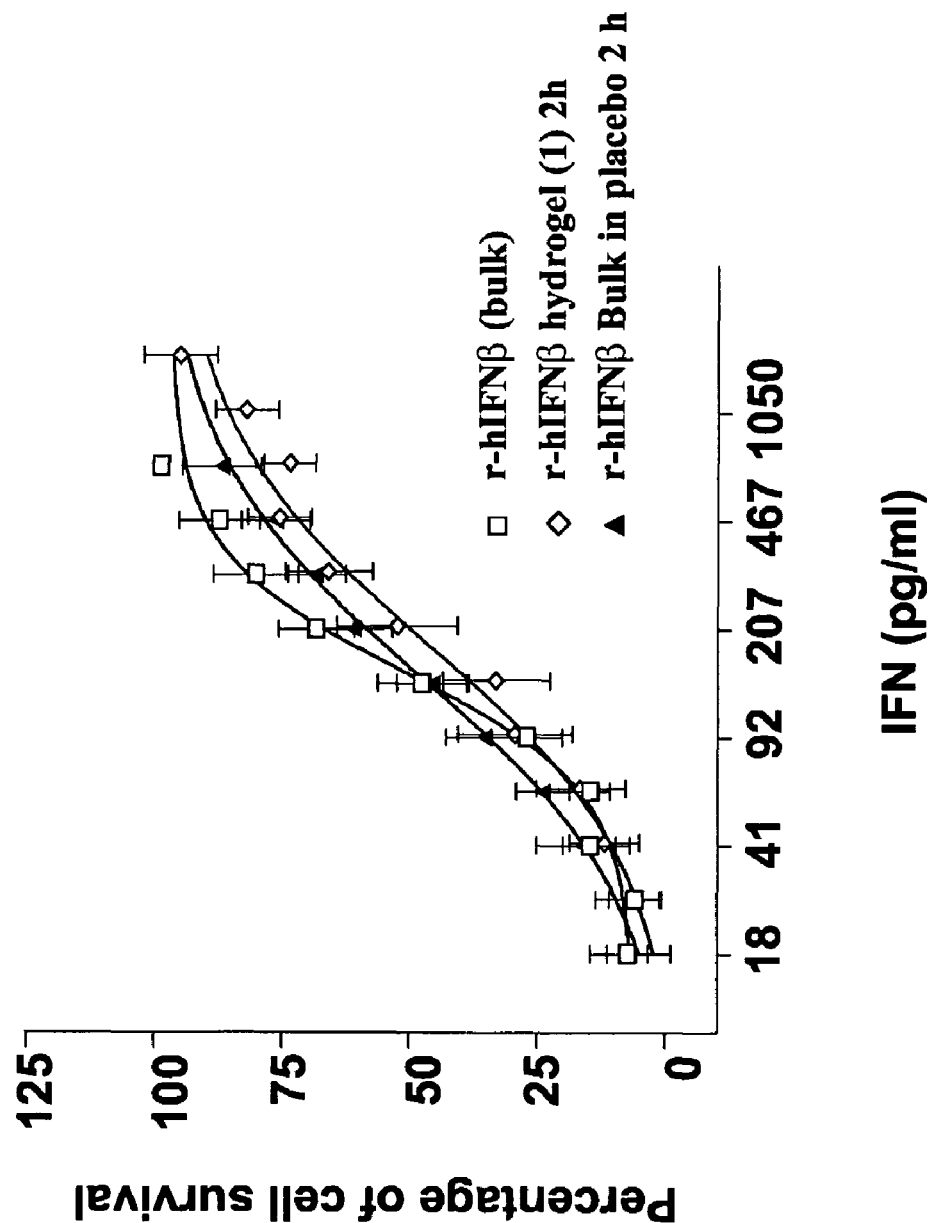
FIG. 2 represents the antiviral activity of r-hIFNβ 1a released after 2 hours from r-hIFNβ 1a-Poloxamer Hydrogel (1) (open lozenges) compared to r-hIFNβ 1a bulk (open squares) and r-hIFNβ 1a bulk co-mixed with Poloxamer gel without r-hIFNβ 1a Placebo) (full triangles). Antiviral activity is expressed by the percentage of cell (WISH cells) survival after VSV infection as a function of r-hIFNβ 1a concentration (Example 2).

The r-hIFN-beta 1a released after 2 hours from both batches showed that the bioactivity was maintained and recovery was complete, as compared to r-hIFN-beta 1a bulk spiked in placebo (FIG. 2). Therefore, it appears that poloxamer hydrogels are capable to retain full r-hIFN-beta 1a biological activity upon drug release.

Example 3

Pharmacokinetic Profile of Poloxamer 407-r-hIFN-beta 1a Hydrogel (1)

In order to test the sustained release characteristics of IFN Poloxamer hydrogel of the invention, the hydrogel pharmacokinetic profile can be compared with that of buffer formulations and other gel formulations.

Pharmacokinetic profile of IFN-beta hydrogel formulation (1), was studied in naïve cynomologus monkeys (2 males and 2 females in each group) and compared to the pharmacokinetic profile of an IFN-beta lipogel formulation.

Samples were provided in pre-filled syringes, equipped with a 19 G needle. The study was designed (Table IV below) to compare a once-a-week s.c. injection of IFN-beta hydrogel (1) (120 µg/ml) with a once-a-week injection of liquid buffered (pH 3.8) formulation of bulk IFN-beta (Control 1) or a once-a-week s.c. injection of IFN-beta lipogel (120 µg/ml) (Control 2).

Another control group was used wherein the monkeys were administered in a three times a week (TIW) fashion (3 s.c. injections separated by 48 hours intervals: t=0, 48 h and 96 h), mimicking the current Rebif® dosing regimen for MS therapy (Control 3).

IFN solution for Control 1 (Group 2) consisted in an 40 µg/mL IFN solution in acetate buffer 50 mM.

IFN-beta lipogel composition for Control 2 (Group 3) was the following:

| | |
|---|---|
| Glycerin monostearate (GMS), (RYLO ™ MG20 PHARMA, Danisco Cultor) | 22.37% w/w |
| PEG400 (Lutrol E400, BASF) | 63.09% w/w |
| Acetic Acid | 4.03% w/w |
| Acetate buffer [50 mM/pH 3.8] | 9.94% w/w |
| r-hIFN beta 1a | 0.01% w/w |
| L-Methionine (Sigma) | 0.03% w/w |
| Hydroxypropyl-β-cyclodextrin (Cavasol W7HP, Wacker) | 0.03% w/w. |

IFN solution for Control 3 (group 4) consisted in 16 µg/mL IFN solution in acetate buffer 50 mM.

Blood sampling included pre-dose, and was designed to cover 14 days after injection (336 h) for Groups 1 and 3; to cover 2 days after injection for Group 2. Sampling for Group 4 was designed to allow PK profiling after the first and last r-hIFN beta 1a injection, and full profiling of neopterin.

r-hIFN beta 1a was quantified by an Enzymatic Immunoassay, ELISA (Fujirebio), as described above. Neopterin levels were quantified by RIA assay (ICN Biomedical).

TABLE IV

Figure 3:
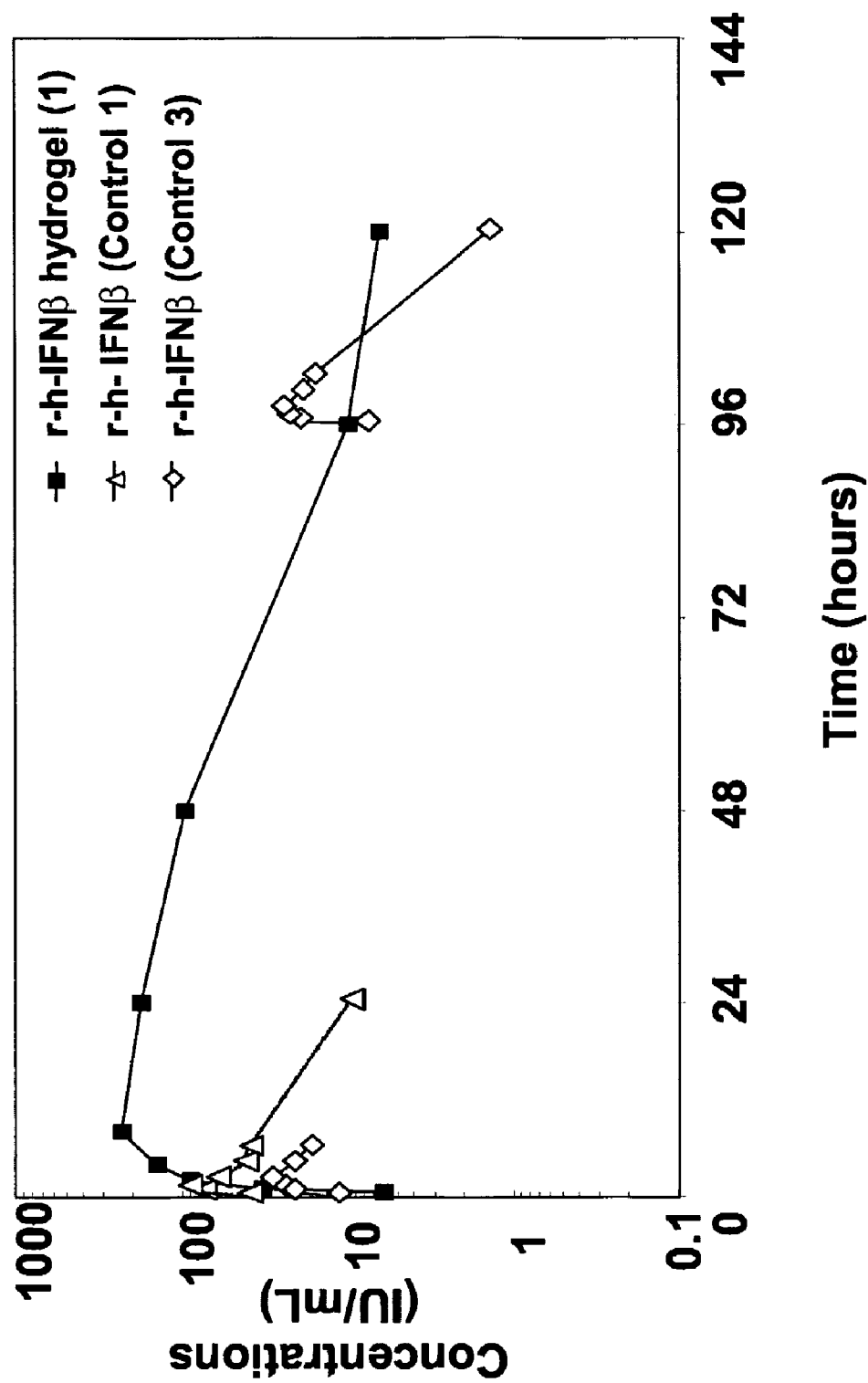
FIG. 3 represents the variation of the blood concentration in r-hIFNβ 1a versus time, in naïve cynomolgus monkeys after subcutaneous injection of either a single injection of 3.6 µg/kg of r-hIFNβ 1a Poloxamer Hydrogel (1) (full squares), a single injection of 3.6 µg/kg r-hFNβ 1a bulk (Control 1: open triangle) or three injections within a week separated by 48 hours intervals (t=0, 48 h and 96 h) of 1.223 µg/kg each (Control 3: open lozenges) (Example 3).

| Group | Formulation Type | Dose (µg/Kg) | Notes |
|---|---|---|---|
| 1 | IFN-beta hydrogel (1) | 3.67 s.c. | Poloxamer hydrogel, injection at t = 0 |
| 2 | IFN-beta (Control 1) | 3.67 s.c. | Bulk solution, injection at t = 0 |
| 3 | IFN-beta lipogel (Control 2) | 3.67 s.c. | Glyceryl monostearate lipogel at t = 0 |
| 4 | Bulk IFN-beta (Control 3) | 3 × 1.223 s.c. | Bulk solution Injections at t = 0, 48 h, 96 h |

β-IFN Release:

Results evidenced that, after a single s.c. injection, Poloxamer hydrogel (1) (Group 1) release r-hIFN beta 1a in a controlled pattern, sustaining plasma levels above 5UI/ml for about a week, and possibly more (FIG. 3).

Protein bioavailability is significantly higher (Table V below) to the buffered liquid formulation (both s.c. single and TIW injection) and lipogel formulation used as controls.

Figure 4:
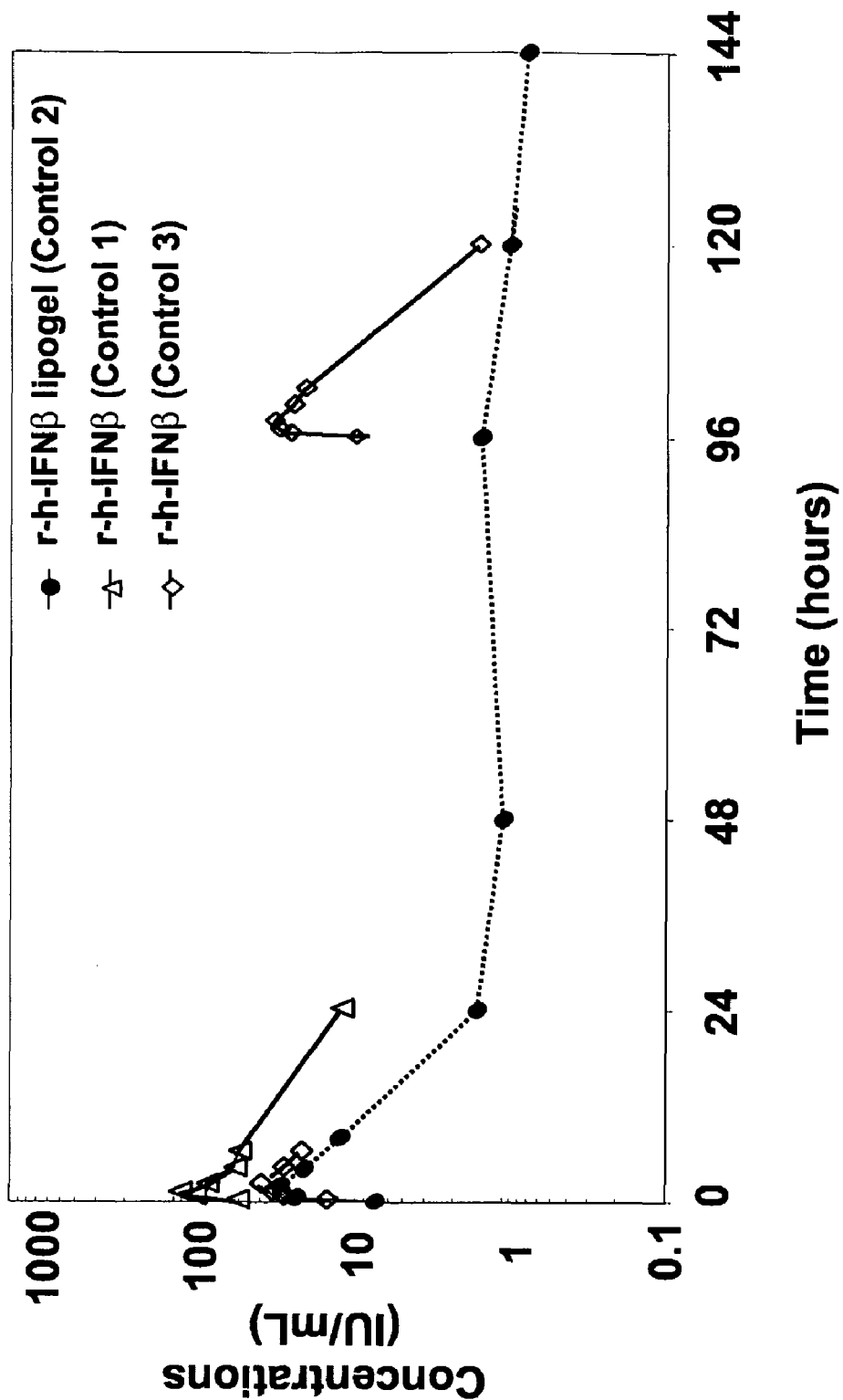
FIG. 4 represents the variation of the blood concentration in r-hIFNβ 1a versus time in naïve cynomolgus monkeys after a single subcutaneous of 3.6 µg/kg of r-hIFNβ 1a GMS lipogel (Control 2: dots) or three injections within a week separated by 48 hours intervals (t=0, 48 h and 96 h) of 1.223 µg/kg each (Control 3: open lozenges) (Example 3).

The r-hIFN beta 1a release for Poloxamer hydrogel (1) shows a real pronounced controlled pattern compared to the r-hIFN beta 1a release profile obtained with GMS based lipogel (Group 3) as shown on FIGS. 3 and 4. r-hIFN beta 1a release profile from the lipogel (Control 2) is characterized by a lower "burst" and a low, prolonged steady state.

These results shows that the lipogel formulation used as Control 2 is not suitable for sustained release of r-hIFN beta 1a.

TABLE V

| PK parameters | IFN-beta Hydrogel (1) | IFN-beta Lipogel (Control 2) | IFN-beta (Control 1) | IFN-beta (Control 3) Day 1 | IFN-beta (Control 3) Day 5 |
|---|---|---|---|---|---|
| T max (h) | 8.0 ± 0.0 | 1.5 ± 0.5 | 1.3 ± 0.5 | 1.8 ± 0.5 | 1.4 ± 0.5 |
| C max (IU/ml) | 231.3 ± 116.4 | 24.0 ± 12.1 | 96.3 ± 53.4 | 31.3 ± 0.9 | 26.1 ± 16.5 |
| T ½ (h) | 19.4 ± 2.4 | 45.1 ± 77.6 | 9.5 ± 3.8 | 6.1 ± 2.8 | 8.0 ± 3.5 |

Serum Neopterin Levels Increase:

Pharmacodynamic (PD) results confirmed the biological activity of r-hIFN beta 1a released from gels. Neopterin levels increased with a $t_{max}$ shift of about 24 hours for hydrogel (1) injection vs. control (Control 1). Repeated dosing (TIW) of r-hIFN beta 1a gave a lower but extended PD profile (Control 3). Lipogel formulation gave a lower pharmakodynamic profile (Control 2).

Preparation of Control Lipogel Formulation:

In a polypropylene becker (low protein adsorption), weighed amounts of GMS and PEG are mixed in acetate buffer [50 mM, pH 4-5] and maintained in a water bath (40° C.) for few minutes in order obtain a molten and homogeneous lipid matrix.

In a different vessel, a small amount of acetate buffer [50 mM, pH 4-5], containing stabilizing agents and excipients (i.e. Cyclodextrin and L-Methionine), is added to a concentrated r-hIFN-beta 1a bulk solution (2 mg/mL). This formulated buffer is first put in a water bath (40° C.) for about 1.5 min and added into the lipid mixture.

The mixture is then left in the water bath for about 5-10 min and then cooled down to r.t. under mild agitation with a polypropylene rod.

These results show that the hydrogel (1) has a similar biological activity as r-hIFN beta 1a control liquid formulations and allows sustaining plasma levels of r-hIFN beta 1a for at least one week and an improved bioavailability.

Example 4

Sterilizing Filtration of Poloxamer 407-r-hIFN-beta 1a Hydrogel (1)

The monophasic hydrogel solution containing IFN-beta could be treated by sterilizing filtration. IFN-hydrogel (1) was prepared as described in Example 1.

Two different membranes (PVDF: polyvinylidene fluoride and PES: polyethersulfone) from PALL Corporation of 47 mm membrane diameter and cut off of 0.2 mm were used at a temperature wherein the viscosity of the solution is kept low, e.g. 4° C.

Viscosity is measured before and after filtration in a Rheometer (ViscoStar L Fungilab): 50 mL of hydrogel (1) into a polypropylene vial, kept in ice bath (T=5±2° C.), spindle n° 2, 100 rpm. No significant rheological changes due to filtration process were observed.

IFN monomer content and release kinetics from IFN loaded hydrogel (1), before and after filtration was analysed by SEC HPLC/fluorescence detector (PBS (pH 7.4), 37° C., 100 rpm/1 g of hydrogel (1) in 4 mL of PBS). Obtained release profiles after filtration are very similar to those before filtration, therefore the filtration process does not modify the IFN release properties of the hydrogel.

Example 5

Poloxamer 407-r-hIFN-beta 1a Hydrogel (2)

IFN-hydrogel (2) was prepared as described in Example 1 and Trehalose (Sigma) 2.6% w/w is added to the buffer solution before the formation of the poloxamer hydrogel solution, i.e. before the addition of Poloxamer 407.

| Hydrogel (2) composition: | |
|---|---|
| Poloxamer 407 | 25% w/w |
| Acetate buffer 50 mM/pH 3.8 | 72.04% w/w |
| r-hIFNbeta 1a | 0.012% w/w |
| L-Methionine | 0.03% w/w |
| Poloxamer 188 | 0.24% w/w |
| Trehalose | 2.6% w/w. |

Viscosity

Dynamic viscosity studies were performed to characterize hydrogel (2) and to characterize its injectability properties. A ViscoStar L Fungilab rotational viscometer was used, obtaining a direct reading of viscosity in mPas (Centipoises). The hydrogel (2) was introduced into a polypropylene vial and viscosity measures (SPL4, speed range 200-300 rpm) were carried out while varying the temperature and continuously reading values on the viscometer display.

Results show a different rheological behavior of hydrogel (2) in comparison with hydrogel (1). The use of Trehalose at 2.6% w/w in the hydrogel of the invention (2) results in the increase in the sol-gel transition temperature (FIG. 5) which improves manufacturing conditions and handling of the matrix.

Example 6

Poloxamer 407-r-hIFN-beta 1a Hydrogel (3)

IFN-hydrogel (3) was prepared as described in Example 1 but Hydroxypropyl-β-cyclodextrin (Cavasol W7HP, Wacker) 2.6% w/w is added to the buffer solution under magnetic stirring (500-700 rpm) before the addition of Poloxamer 407. Then, Poloxamer 407 is added to the Hydroxypropyl-β-cyclodextrin/buffer solution as described in Example 1, under magnetic stirring.

| Hydrogel (3) composition: | |
|---|---|
| Poloxamer 407 | 20% w/w |
| Acetate buffer 50 mM/pH 3.8 | 77.34% w/w |
| r-hIFNbeta 1a | 0.015% w/w |

-continued

| Hydrogel (3) composition: | |
|---|---|
| L-Methionine | 0.04% w/w |
| Cavasol W7HP | 2.6% w/w. |

Viscosity

Dynamic viscosity studies were performed to characterize hydrogel (3) and to characterize its injectability properties. A ViscoStar L Fungilab rotational viscometer was used, obtaining a direct reading of viscosity in mPas (centipoises). The hydrogel (3) was introduced into a polypropylene vial and viscosity measures (SPL4, speed range 200-300 rpm) were carried out while varying the temperature and continuously reading values on the viscometer display.

Figure 5:
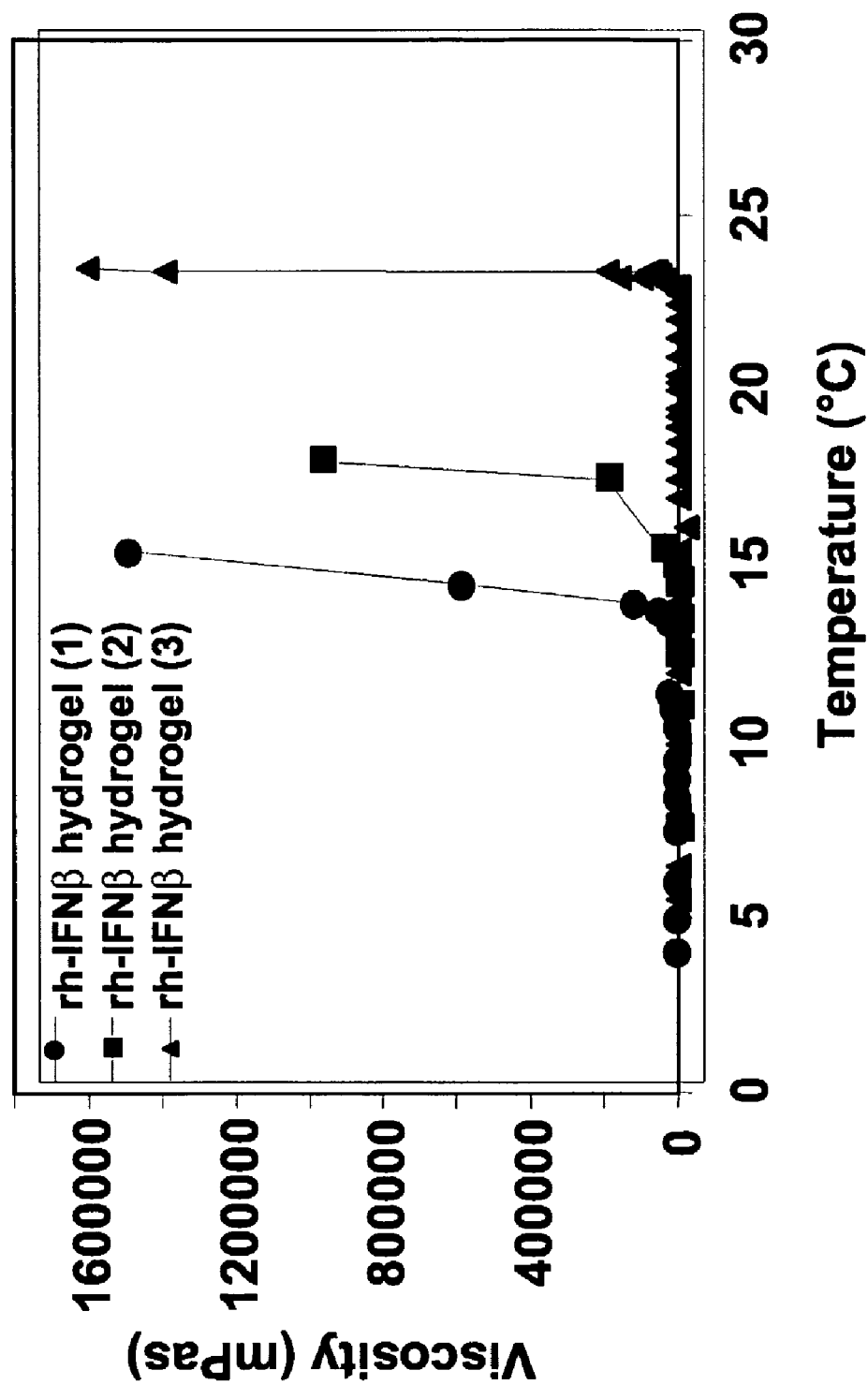
FIG. 5 represents viscosity profiles of Lutrol hydrogel formulation (1)—dots—compared to Lutrol hydrogel formulation containing 2.6% w/w of Trehalose (2)—full squares—and Lutrol hydrogel formulation containing 2.6% w/w HPbetaCD (3)—full triangles.

Results displayed on FIG. 5, show a different rheological behavior of hydrogel (3) in comparison with hydrogel (1): the sol-gel transition temperature of the hydrogel (3) is increased from about 11° C. to 23° C.

Surprisingly, the shift of sol-gel transition temperature of hydrogel (3) is even more significantly increased compared to that of the hydrogel containing Trehalose (2), in spite of a lower concentration of matrix-forming Poloxamer 407 (20% w/w) used (FIG. 5), which improves significantly manufacturing conditions and handling of the matrix.

Protein Release

To simulate physiological subcutaneous conditions, IFN-beta release from hydrogel (3) was investigated in PBS as previously described. Drug release test were performed using 1 g of hydrogel (3) (dispensed using pre-filled syringes) into 4 mL of PBS pH 7.4 at 37±2° C. (shaker bath speed=100 rpm). Samples collected at: 5, 15, 30 minutes, 1 and 2 hours.

Figure 6:
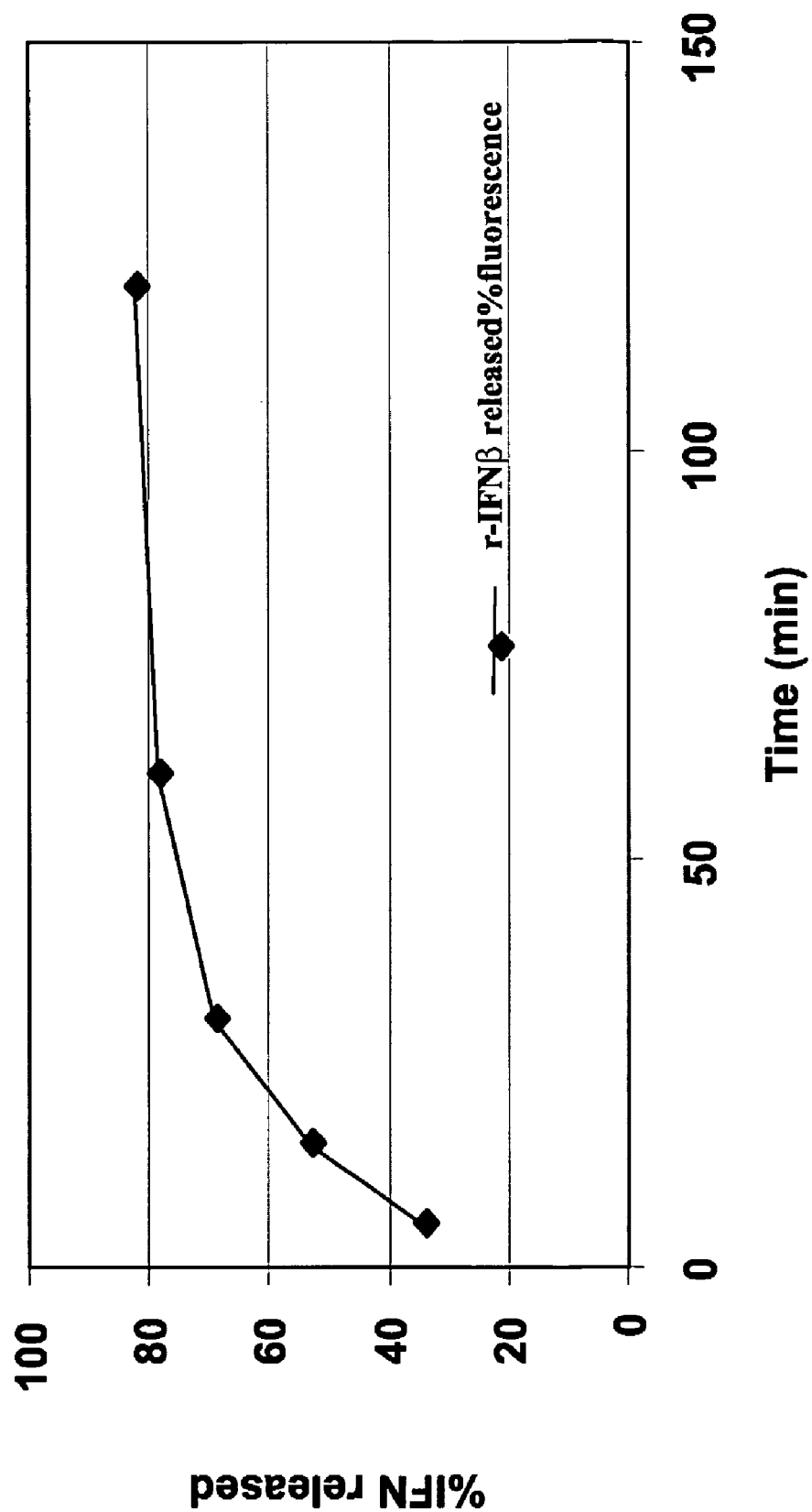
FIG. 6 represents the percentage of r-hIFNβ 1a released from the r-hIFNβ 1a Poloxamer Hydrogel (3) (Poloxamer 407-20% w/w; Acetate buffer 50 mM/pH 3.8-77.34% w/w, r-hIFNβ 1a—0.015% w/w, L-Methionine—0.04% w/w and Hydroxypropyl-β-Cyclodextrin-2.6% w/w) in PBS at pH 7.4 at 37° C. measured by SE-HPLC/fluorescent detector.

Each sample was analyzed by SE-HPLC with fluorescent detector (Trp fluorescence). The sustained release properties (IFN-beta release profile) of the cyclodextrin-containing hydrogel (3) are comparable to those of a hydrogel without a sol-gel temperature transition modifier, i.e. hydrogel (1), despite the shift in the sol-gel transition temperature (FIG. 6). From the antiviral assay as described in Example 2, it was observed that the r-hIFNβ 1a released after 2 hrs the cyclodextrin-containing hydrogel (3) maintained the bioactivity, and recovery was complete, as compared to r-hIFNβ 1a bulk spiked in placebo. Therefore, it appears that the cyclodextrin-containing hydrogel (3) is capable to retain full r-hIFNβ 1a biological activity upon drug release.

Example 7

Poloxamer 407-r-hIFN-beta 1a Hydrogel (4)

IFN-hydrogel (4) was prepared as described in Example 1 and Glycerol 30° Bé (Carlo Erba) 2.6% w/w was added to the buffer solution before the formation of the poloxamer hydrogel solution, i.e. before the addition of Poloxamer 407.

| Hydrogel (4) composition: | |
|---|---|
| Poloxamer 407 | 25% w/w |
| Acetate buffer 50 mM/pH 3.8 | 72.04% w/w |
| r-hIFNbeta 1a | 0.012% w/w |
| L-Methionine | 0.03% w/w |
| Poloxamer 188 | 0.24% w/w |
| Glycerol 30° Bé | 2.6% w/w. |

Example 8

Poloxamer 407-r-hIFN-beta 1a Hydrogel (5)

IFN-hydrogel (5) was prepared as described in Example 1 and PEG (Lutrol®E400, Basf) 2.6% w/w was added to the buffer solution before the Formation of the poloxamer hydrogel solution, i.e. before the addition of Poloxamer 407.

| Hydrogel (5) composition: | |
|---|---|
| Poloxamer 407 | 25% w/w |
| Acetate buffer 50 mM/pH 3.8 | 72.04% w/w |
| r-hIFNbeta 1a | 0.012% w/w |
| L-Methionine | 0.03% w/w |
| Poloxamer 188 | 0.24% w/w |
| PEG(Lutrol ®E400) | 2.6% w/w. |

Example 9

Syringing Test

In order to test the subcutaneous injectability of IFN poloxamer based hydrogels, a syringing test can be performed using different types of needles.

In particular, the syringing test is performed using a new injection technology, called Depot One (Imprint Pharmaceuticals)

Selected Depot One needles are the following:
  18/23 (internal diameter equivalent to a 18 gauge needle and minimum external diameter of a 21 gauge needle)
  21/26 (internal diameter equivalent to a 21 gauge needle and minimum external diameter of a 26 gauge needle).

3 mL polypropylene syringes are loaded with 0.5 mL of hydrogel (1) or hydrogel (3) (kept at 4° C.) and after about 15 minutes at room temperature are discharged in a polystyrene vial. The "needle performance" is estimated on the basis of the force required to discharge the syringes.

The syringing tests at room temperature show that hydrogel (3) has very good syringing characteristics at room temperature.

Example 10

Pharmacokinetic Profile of Poloxamer 407-r-hIFN-β 1a Hydrogel (3)

The pharmacokinetic characteristics of Poloxamer 407-r-hIFN-beta 1a Hydrogel (3) can be assessed in male cynomolgus monkeys (Captive bred *Macaca fascicularis*) naïve to any previous r-hIFN-beta and other research drug treatment.

Animals:
Body weight range: 24 kg at study initiation
Age range: approximately 5 years
Number of animals per group: 4

The formulations are administered to the animals that have been fasted overnight (i.e. for about 16 hours) before administration. Food will be allowed again 4 hours after treatment. Water will be allowed "ad libitum".

r-hIFN-β1a-hydrogel formulation (3) is prepared in pre-filled syringes of 320 mg each with 21G needle at strength of 174 μg r-hIFNβ 1a per gram. Due to the thermo-reversible nature of the gel formulation, pre-filled syringes should be stored at 4° C. and maintained at room temperature only the time needed for the administration.

A single dose is 44 μg of r-hIFNβ 1a per animal is injected in the subcutis of one of the legs. 200-250 mg of one r-hIFN-beta 1a hydrogel formulation (3) pre-filled syringe are administered to each monkey (one syringe for each monkey) in Group 1 (animals 1 to 4). Glass pre-filled syringes are weighed before and after the administration to allow the exact evaluation of administered dose.

Blood is collected from a cephalic vein into tubes, according to the scheme detailed in the table below:

| Sampling time | Blood sampling IFN beta analysis | Blood sampling Neopterin analysis | Total amount of blood collected |
|---|---|---|---|
| Pre-study (day −1) | — | X | 0.5 mL |
| Pre-dose (0 h) | X | X | 1.5 mL |
| 30 min | X | — | 1.0 mL |
| 1 h | X | — | 1.0 mL |
| 2 h | X | — | 1.0 mL |
| 4 h | X | — | 1.0 mL |
| 6 h | — | X | 0.5 mL |
| 8 h | X | — | 1.0 mL |
| 24 h | X | X | 1.5 mL |
| 32 h | X | X | 1.5 mL |
| 48 h | X | X | 1.5 mL |
| 56 h | X | X | 1.5 mL |
| 72 h | X | X | 1.5 mL |
| 96 h | X | X | 1.5 mL |
| 104 h | X | X | 1.5 mL |
| 120 h | X | X | 1.5 mL |
| 168 h | X | X | 1.5 mL |

Blood samples are allowed to clot for 60 minutes at room temperature. The clot is spun down by centrifugation at 2 500 g (3 350 rpm) at 4° C. for 15 minutes.

When 0.5 mL of blood is collected, 2 serum aliquots are prepared, the 1$^{st}$ with at least 0.125 mL of serum, the 2$^{nd}$ with the remaining serum.

When 1.0 mL of blood is collected, 2 serum aliquots are prepared, the 1$^{st}$ with at least 0.250 mL of serum, the 2$^{nd}$ with the remaining serum.

When 1.5 mL of blood is collected, 3 serum aliquots are prepared, the 1$^{st}$ and the 2$^{nd}$ with at least 0.250 mL of serum, the 3$^{rd}$ with the remaining serum.

Serum samples for r-hIFN-beta 1a analysis are stored at −80° C.

Serum samples for Neopterin analysis are stored at −20° C.

The following pharmacokinetic parameters are obtained from the individual serum concentrations of r-hIFNβ 1a (as IU/mL) vs. time (as hours) after each administration:

Directly by Observation:
Cmax: The highest concentration value found in serum
Tmax: The time from administration at which the Cmax value is found
Tz: The last sampling time at which a quantifiable concentration is found
CZ: The concentration value obtained at sampling time Tz.

By the WinNonlin® Program:
AUCz: The area under the serum concentration vs. time curve up to sampling time Tz, calculated by the log-linear trapezoidal rule (linear up to the Cmax, logarithmic after the Cmax).
Tlin: The first point considered for the determination of the elimination half-life.
λz: The elimination rate constant, calculated by the slope of the linear regression curve obtained by fitting the natural logarithms of the terminal concentration values vs. time (from Tlin to Tz).

t½: The elimination half-life, calculated by the equation:

$$t^{1/2} = (\ln 2)/\lambda z$$

AUC: The area under the serum concentration vs. time curve, calculated by the following equation:

$$AUC = AUCz + Cz/\lambda z$$

% AUCext: The percentage of AUC extrapolated (i.e. obtained by extrapolation), calculated by the following equation:

$$\% AUCext = (AUC - AUCz)/AUC \cdot 100$$

This experiment can be performed with a parallel Group 2 of animals using a marketed IFNβ formulation as a reference (such as Rebif®: a solution formulation containing human serum albumin (HSA), mannitol and sodium acetate as excipients packaged in pre-filled syringes with 21 G needle of 0.5 mL injection volume at a strength of 44 μg r-hIFNβ 1a (12 MIU). In this case, the entire content (0.5 mL) of one Rebif® pre-filled syringe is administered to each monkey (one syringe per animal) in Group 2 (animals 5 to 8).

Analyte: Interferon Beta (r-hIFNβ 1a):

| | Tmax [h] | Cmax [IU/mL] | AUClast [hr*IU/mL] | Tlast [h] | Clast [IU/mL] | $AUC_{(0-72)}$ [hr*IU/mL] |
|---|---|---|---|---|---|---|
| Mean | 12 | 1930 | 54300 | 96 | 9.64 | 53900 |
| SD | 8.0 | 992 | 16000 | 16 | 5.10 | 15800 |
| CV % | 67 | 51.3 | 29.4 | 17 | 52.9 | 29.3 |

These results show that r-hIFNβ 1a hydrogel formulation (3) has a high bioavailability.

The invention claimed is:

1. A pharmaceutical composition comprising:
  a) an interferon (IFN);
  b) a poloxamer hydrogel selected from Poloxamer 407 or Poloxamer 338;
  c) an antioxidant;
  d) a surfactant;
  e) a solution-to-gel temperature transition modifier at a concentration of about 1% to about 3%; and
  f) a buffer.

2. The composition according to claim 1 wherein the interferon is IFN-beta.

3. The composition according to claim 2, wherein the interferon is recombinant IFN-beta.

4. The composition according to claim 3, wherein the interferon is recombinant IFN-beta 1a.

5. The composition according to claim 1, wherein the solution-to-gel temperature transition modifier is trehalose or cyclodextrin.

6. The composition according to claim 1, wherein the poloxamer hydrogel is Poloxamer 407.

7. The composition according to claim 6, wherein the composition comprises 20 to 25% w/w of Poloxamer 407.

8. The composition according to claim 1, wherein said composition comprises:
  a) 10-800 μg/mL interferon;
  b) 20%-30% (w/w) poloxamer hydrogel;
  c) antioxidant at 100 to 800 fold molar excess (with respect to said interferon);
  d) about 0.01 mg/mL to about 10 mg/mL surfactant;
  e) about 1% to about 3% (w/w) solution-to-gel modifier; and
  f) a buffer.

9. The composition according to claim 8, wherein the surfactant comprises about 0.01 mg/mL to about 10 mg/mL Poloxamer 188.

10. The composition according to claim 9, wherein the composition further comprises trehalose as a solution-to-gel modifier.

11. The composition according to claim 8, wherein the composition comprises hydroxypropyl beta cyclodextrin as a solution-to-gel modifier.

12. A method of treating multiple sclerosis comprising a step of administering a composition according to claim 1 to an individual in need of treatment.

13. The composition according to claim 1, wherein the solution-to-gel temperature transition modifier is trehalose.

14. The composition according to claim 1, wherein the solution-to-gel temperature transition modifier is cyclodextrin.

15. The composition according to claim 1, wherein the solution-to-gel temperature transition modifier is present at a concentration of about 2.6% (w/w).

16. A composition comprising:
   a) Poloxamer 407—25% w/w
      Acetate buffer 50 mM/pH 3.8—74.7% w/w
      r-hIFNbeta 1a—0.012% w/w
      L-Methionine—0.03% w/w
      Poloxamer 188—0.24% w/w;
   b) Poloxamer 407—25% w/w
      Acetate buffer 50 mM/pH 3.8—72.04% w/w
      r-hIFNbeta 1a—0.012% w/w
      L-Methionine—0.03% w/w
      Poloxamer 188—0.24% w/w
      Glycerol—2.6% w/w;
   c) Poloxamer 407—25% w/w
      Acetate buffer 50 mM/pH 3.8—72.04% w/w
      r-hIFNbeta 1a—0.012% w/w
      L-Methionine—0.03% w/w
      Poloxamer 188—0.24% w/w
      PEG—2.6% w/w;
   d) Poloxamer 407—25% w/w
      Acetate buffer 50 mM/pH 3.8—72.04% w/w
      r-h-IFNbeta 1a—0.012% w/w,
      L-Methionine—0.03% w/w
      Poloxamer 188—0.24% w/w
      Trehalose—2.6% w/w; or
   e) Poloxamer 407—20% w/w
      Acetate buffer 50 mM/pH 3.8—77.34% w/w
      r-h-IFNbeta 1a—0.015% w/w
      L-Methionine—0.04% w/w
      Hydroxypropyl-$\beta$-Cyclodextrin—2.6% w/w.

17. A method for preparing an IFN hydrogel composition comprising adding a calculated amount of poloxamer hydrogel selected from Poloxamer 407 or Poloxamer 338 to a buffered solution at a temperature wherein a homogeneous polymer solution is formed and then adding an interferon.

18. The method according to claim 17, wherein the buffer solution contains about 1% to about 3% (w/w) solution-to-gel temperature transition modifier.

19. The method according to claim 17, wherein the buffer solution contains a solution-to-gel temperature transition modifier selected from trehalose and cyclodextrin.

20. The method according to claim 17, wherein the interferon is added from an interferon solution comprising interferon and stabilizers selected from L-methionine, Poloxamer 188 or a combination thereof.

* * * * *

UNITED STATES PATENT AND TRADEMARK OFFICE
CERTIFICATE OF CORRECTION

PATENT NO. : 7,879,320 B2
APPLICATION NO. : 11/596599
DATED : February 1, 2011
INVENTOR(S) : Del Curto et al.

It is certified that error appears in the above-identified patent and that said Letters Patent is hereby corrected as shown below:

Column 5,
Lines 41-42, "intramuscularly" should read --intra-muscularly--.
Line 67, "/NTBSC)." should read --/NIBSC).--.

Column 11,
Lines 49-50, "150         should read   --150 µg/mL).
             Methionine can"                Methionine can--.

Column 17,
Line 39, "(millipascal" should read --(milliPascal--.
Line 63, "becker" should read --beaker--.

Column 22,
Line 65, "results shows" should read --results show--.

Column 23,
Line 24, "becker" should read --beaker--.
Line 27, "for few minutes in order obtain" should read --for a few minutes in order to obtain--.

Column 30,
Line 6, "Poloxamer 407—25% w/w" should read --d. Poloxamer 407—25% w/w--.

Signed and Sealed this
Thirty-first Day of May, 2011

David J. Kappos
*Director of the United States Patent and Trademark Office*